United States Patent [19]

Smith

[11] Patent Number: 4,550,035

[45] Date of Patent: Oct. 29, 1985

[54] COSMETIC APPLICATOR USEFUL FOR SKIN MOISTURIZING AND DEODORIZING

[75] Inventor: James A. Smith, Old Tappan, N.J.

[73] Assignee: Creative Products Resource Associates, Ltd., Clifton, N.J.

[21] Appl. No.: 605,054

[22] Filed: Jun. 28, 1984

Related U.S. Application Data

[62] Division of Ser. No. 448,806, Dec. 10, 1982, Pat. No. 4,462,981.

[51] Int. Cl.[4] .................... A47K 7/02; A47K 7/03; B32B 5/18
[52] U.S. Cl. .................... 427/398.1; 427/395; 424/27; 424/28; 252/90; 252/91
[58] Field of Search .............. 424/27, 28; 252/90, 252/91; 427/398.1, 316, 395

[56] References Cited

U.S. PATENT DOCUMENTS

| | | | |
|---|---|---|---|
| 2,033,758 | 3/1936 | Cronan et al. | 36/71 |
| 2,061,911 | 11/1936 | Leindorf | 36/43 |
| 2,495,066 | 1/1950 | Jones | 15/208 |
| 3,283,357 | 11/1966 | Decker et al. | 424/27 |
| 3,464,413 | 9/1969 | Goldfarb et al. | 128/268 |
| 3,567,118 | 3/1971 | Shepherd et al. | 239/6 |
| 3,657,760 | 4/1972 | Kudisch | 424/28 X |
| 3,691,270 | 9/1972 | Charle et al. | 424/28 X |
| 3,703,481 | 11/1972 | Barker et al. | 424/28 |
| 3,795,624 | 3/1974 | Feinstone | 252/91 |
| 3,818,533 | 6/1974 | Scheuer | 427/395 |
| 3,842,519 | 10/1974 | Lapidus | 36/44 |
| 3,852,897 | 12/1974 | Bridge | 36/44 |
| 4,137,345 | 1/1979 | Falivene | 427/398.1 X |
| 4,257,176 | 3/1981 | Hartung et al. | 36/44 |
| 4,344,930 | 8/1982 | MacRae et al. | 424/28 |

*Primary Examiner*—George F. Lesmes
*Assistant Examiner*—Nancy A. B. Swisher
*Attorney, Agent, or Firm*—Kenyon & Kenyon

[57] ABSTRACT

The present invention relates to cosmetic applicators comprising absorbent sheets impregnated with a mixture of emollients, absorbent particles, fragrances and deodorizing agents which are useful for moisturizing and deodorizing wetted or sweaty skin surfaces, and are especially useful for foot deodorizing and moisturizing.

6 Claims, No Drawings

COSMETIC APPLICATOR USEFUL FOR SKIN MOISTURIZING AND DEODORIZING

This is a division of application Ser. No. 448,806 filed Dec. 10, 1982, now U.S. Pat. No. 4,462,981.

BACKGROUND OF THE INVENTION

The present invention relates to cosmetic applicators comprising absorbent sheets impregnated with a mixture of emollients, absorbent particles, fragrances and deodorizing agents which are useful for moisturizing and deodorizing wetted or sweaty skin surfaces, and are especially useful for foot deodorizing and moisturizing.

The problems associated with the manufacture of fabrics impregnated with odorizing, deodorizing, sanitizing and cleansing materials is generally discussed in U.S. Pat. No. 3,567,118, which discloses composite fibers which are impregnated with such agents dispersed in a hydrophilic acrylate or methacrylate carrier. Such impregnated paper sheets are disclosed to be useful for shoe insoles, bandages, cosmetic facial tissues and for disposable household cleaning towels.

It is an object of the present invention to provide a cosmetic applicator which will function to moisturize and deodorize skin, particularly wetted skin, when it is pressed or rubbed against the skin.

It is another object of the present invention to provide a cosmetic applicator which will deliver moisture and oil absorbent particles to the skin which function to absorb excess moisture and oils present due to perspiration.

It is another object of the present invention to provide a cosmetic applicator adapted to deliver antifungal and antibacterial substances to the skin.

Other objects, advantages and novel features of the present invention will be apparent to those skilled in the art from the following description and appended claims.

BRIEF DESCRIPTION OF THE INVENTION

The objects of the present invention are attained by providing a cosmetic applicator comprising a sheet of absorbent material having interstices therein. The interstices are impregnated with a composition comprising a mixture of oily emollients, particles of absorbent agents, deodorizing agents and fragrances. Effective amounts of antifungal and antibacterial agents may also be employed in the impregnating composition. The ingredients of the composition are selected so that an effective amount of emollient, absorbent, deodorizer, fragrance and, optionally, antifungal and/or antibacterial is released and coated onto the skin when the impregnated sheet is pressed or rubbed against a moist skin surface.

DETAILED DESCRIPTION OF THE INVENTION

The cosmetic applicator of the present invention comprises a sheet of porous material which is impregnated with a composition adapted to be released when the sheet is rubbed or pressed against the skin so as to moisturize and deodorize it. The impregnation of the interstices of the sheet with the composition is preferably carried out to the extent that the sheet is overcoated with the composition. This overcoating assures that sufficient composition will be available to perform the cosmetic functions of the invention, and also increases the ease of transfer of the composition to the skin surface as the sheet is rubbed or pressed against it. Furthermore, certain components of the composition are selected so that they will solubilize in any moisture present on the skin surface, thus further enhancing the transfer of the moisturizing and deodorizing properties of the applicator. However, the finished cosmetic applicators are substantially dry and non-sticky to the touch, even when comprising an overcoating of composition.

The compositions useful in the present invention are formulated so as to comprise a large proportion, preferably 30–65%, of one or more solid, water-insoluble absorbent agents such as particles of talc, soy or oat protein, starch, kaolin, silica gel, puffed borax, zeolites or the like. Preferably a major proportion of moisture absorbing particles such as those of puffed borax, talc or zeolite are used in conjunction with a minor proportion of oil absorbing particles such as those of colloidal soy or oat protein. Preferred moisture absorbing particles for use in the compositions of the present invention are those of Supra Talc ® No. 1705, available from Cyprus Industrial Minerals, Englewood, Colo. The particles are loosely held in and on the porous sheet by the liquid or waxy components of the composition and are deposited on the skin when the sheet is applied thereto under pressure, as when the sheet is rubbed over the skin. The absorbent particles thus are made available to absorb the oily and aqueous components of any perspiration which may be present, as well as to absorb any excess moisture which may have remained on the skin after washing. The particles also adhere to the skin so as to continue to absorb excess perspiration and so as to perform a continuing drying and deodorizing function.

The impregnated composition also comprises a large proportion, preferably 30–60%, of emollients. The emollients or moisturizers, effective in the present invention function for the prevention and relief of skin dryness and for the protection of the skin against chapping, chemical irritants and the like. Emollients useful in the practice of the present inventions are generally described by G. Barnet, Emollient Creams and Lotions, in *Cosmetics—Science and Technology,* Wiley Interscience Pub. (1957) at pages 99–146, and by S. J. Strianze, Hand Creams and Lotions, in *Cosmetics—Science and Technology,* at pages 147–181.

The compositions of the present invention preferably include one or more emollients selected from each of three classes of emollients: (1) emollient oils, (2) emollient waxes, and (3) nonionic emollients.

The amount of each class of emollient which may be employed in the compositions of the present invention may be varied over a wide range, with the total of the emollients being about 30–60% by weight of the composition.

Emollient oils generally function to lubricate the skin surface and to prevent evaporative loss of skin moisture supplied by underlying tissues. They also function to provide a protective barrier against environmental irritants. The emollient oils useful in the practice of the present invention include those commonly employed in emollient creams and lotions, such as liquid hydrocarbons (petrolatum, mineral oil, and the like) vegetable and animal fats and oils (lanolin and its derivatives, triglycerides and the like), alkyl fatty acid esters (methyl, isopropyl, and butyl esters of fatty acids, and the like), fatty alcohol esters of benzoic acid, phospholipids and their derivatives (lecithin, cephalin and the like) and silicones. In the practice of the present invention, silicone oils are preferred and may consist of one or more of the commercially-available tetrameric or pentameric cyclic silicones or of methyl or phenyl polysiloxanes, i.e., polydimethylsiloxane or mixed methyl/phenyl polysiloxanes. Preferred cyclic silicone oils include Dow Corning ®344 or 345 Fluid (Dow-Corning, Midland, Mich.) which are tetrameric and pentameric polydimethyl cyclosiloxane, respectively. Emollient oils will preferably form about 10–35% by weight of the composition. Another preferred emollient oil is a mixture of $C_{12}$–$C_{15}$ linear primary alkyl esters of benzoic acid which is described in U.S. Pat. No. 4,275,222, which is incorporated by reference herein, and which is commercially-available from Finetex, Inc., Elmwood Park, N.J. as Finsolv TN ®. Such esters function to impart a non-sticky, talc-like feel to skin surfaces.

Emollient waxes function to soften and smooth the skin surface, prevent evaporation of interior skin moisture, to adjust to final viscosity of the composition. The emollient waxes useful in the practice of the present invention include beeswax, spermaceti, solid hydrocarbons, $C_{12}$–$C_{18}$ fatty alcohols, glyceryl monostearate, ethylene glycol monostearate, polyethylene glycol distearate and other $C_{12}$–$C_{18}$ fatty acid-$C_2$–$C_5$ polyol esters. Particularly useful in the practice of the present invention are mixtures of fatty alcohols, such as lauryl, cetyl, oleyl and stearyl alcohols and the fatty acid-polyol esters, i.e., pentaerythritol tetrastearate. Preferably, emollient waxes will make up about 10–20% of the composition.

Nonionic emollients useful in the compositions of the present invention act to solubilize and emulsify the component mixtures, as well as to moisturize the skin. Preferred nonionic emollients are the polyoxyethylene-polyoxypropylene- or mixed poly-$C_2$–$C_3$ alkoxy-fatty alcohol ethers, such as the cetyl, stearyl, oleyl or lauryl ethers of ethylene oxide or propylene oxide polymers. The mole ratio of alkanoloxy units to alkanol is preferably adjusted so that the ether will be soluble in both alcohol and water. Water-soluble ethers of this type are disclosed in British Pat. No. 1,429,143, the disclosure of which is incorporated herein by reference. These ethers readily solubilize in the moisture present on wet skin, thus exerting the desired emollient effect, as well as assisting the transfer of the other components of the composition. A particularly preferred nonionic emollient is Procetyl AWS ® (Croda, Inc., New York, N.Y.) an alcohol/water-soluble cetyl poly-$C_2$-$C_3$-alkoxylate (CTFA name: PPG 5 Ceteth 20). Preferably nonionic emollients will make up about 1.5–5% by weight of the composition.

Cationic emollients are useful as optional components of the composition of the present invention since they will also solubilize when the applicator is rubbed or pressed against wetted skin surfaces, and thus will be readily transferred to and deposited on the skin surface, so as to exert the desired emollient action.

Cationic emollients useful in the compositions of the present inventions fall generally within the class of cationic surface-active agents. Cationic emollients aid in adhering the emollient mixtures onto the negatively charged surface of the skin, and also function as skin conditioners. When the impregnated sheet is pressed or rubbed against wet skin, a portion of these emollients solubilizes and is readily transferred to the oppositely-charged skin surface, thus imparting their softening and conditioning effect. Cationic emollients are based on the quaternary ammonium, morpholinium, pyridinium, and imidazolinium salts of $C_{12}$–$C_{18}$ fatty acids and amines or their alkanoloxy derivatives. A preferred cationic emollient is Necon CPS-100 ® (Alzo, Inc., Matawan, N.J.), an bis-oleoylethanoloxy-substituted-tallow amine hydrogen phosphate salt wherein the tallow portion of the molecule is a mixture of $C_{14}$–$C_{18}$ alkyls and about 5–8 ethanoloxy units are present in each amine substituent. When employed, cationic emollients may make up about 0.25–2% by weight of the composition, preferably 0.5–1.5%.

The compositions of the present invention also include minor but effective amounts of deodorizing agents and fragrance, preferably about 0.5–15.0 percent by weight of each, most preferably about 0.5–5.0 percent by weight of each, which are useful to counteract and mask perspiration odor, respectively. Deodorizing agents are selected which will solubilize when the cosmetic applicator is rubbed or pressed against a wet skin surface so that an effective amount of the agent is coated onto the skin surface. The preferred deodorizing agent for use in the compositions of the present invention is zinc ricinoleate which is commercially available as Grillocin H4-77 (Rita Chemical Co., Crystal Lake, Ill.), but any of the water-soluble deodorant or antiperspirant salts commonly used in cosmetic preparations may be employed in the practice of the present invention, such as the salts of aluminum and zinc with anions such as sulfate, chloride, chlorohydroxide, phenolsulfonate, basic formate, lactate and sulfamate. For example, aluminochlorhydroxide, basic aluminum bromide, iodide or nitrate, aluminum hydroxy chloride, zirconyl hydroxyl oxychloride or mixtures thereof may be employed as deodorizing agents in the present compositions.

Likewise, any of the fragrances commonly used in cosmetic preparation to mask perspiration odor may be employed in the practice of the present invention. Useful fragrances include, for instance, floral oils such as rose oil, lilac, jasmine, wisteria, apple blossom, or compounded bouquets such as spice, aldehydic, woody, oriental, and the like. A preferred fragrance is K-9100 ® fragrance (Roure DuPont, Teaneck, N.J.).

Minor but effective amounts of antibacterial preservatives are also preferably employed in the compositions of the present invention. Preferably about 0.05–1.0 percent by weight of the composition will consist of one or more preservatives, which are employed in an amount effective to inhibit bacterial growth in the applicator, either during storage or after wetting during use. Any of the preservatives commonly used in cosmetic formulations may be employed in the compositions of the present invention. A particularly useful class of preservatives is the 4-hydroxy-benzoate esters, i.e., the $C_1$–$C_4$ lower alkyl- or benzyl-4-hydroxy-benzoates.

The compositions of the present invention may optionally include up to 10 percent of an effective amount of an antifungal agent which functions to prevent athlete's foot and other fungal skin diseases. Useful fungicides include undecylenic acid, bis(tri-n-alkyltin sulfosalicylates) (U.S. Pat. No. 3,279,986) and N-trichloromethylthio-4-cyclohexene-1,2-dicarboximide, which is commercially available from R. T. Vanderbuilt, Inc., Norwalk, Conn. as Vancide ®89.

Therefore, preferred compositions useful in the present invention may be formulated so as to contain about 30–65% by weight of absorbent particles, 0.5–15% by weight of fragrance, 0.5–15% by weight of deodorizing agents, and 30–60% by weight of a mixture of emollients consisting of 10–35% of one or more emollient oils, 0.5–5% of one or more nonionic emollients, 10–20% of one or more emollient waxes and 0–2% of one or more cationic emollients based on the weight of the composition.

The compositions of the present invention are generally prepared by melting together the emollient waxes, nonionic and cationic emollients, deodorizing agents and optionally, the preservatives and antifungal agents with stirring or shaking at temperatures in the range of about 60°–75° C. The emollient oils, i.e., the silicone oils, and then the absorbent particles are sequentially mixed in. The reaction mixture is slightly cooled, i.e., to about 55°–65° C., and the fragrance is added. The reaction mixture is then allowed to cool to about 50°–55° C.

The finished composition is then applied to the desired weight onto one or both sides of an absorbent sheet which has preferably been warmed to about 50°–55° C. Any method of fabric or foam coating known in the art may be employed. For example, the composition may be coated onto a fabric or paper sheet by means of a Meyer Rod, a floating knife or doctor blade, or may be rolled onto a foam sheet via a stainless steel roller, or applied by spraying.

The absorbent sheets useful in the practice of the present invention may be formed from any flexible material which contains interstices capable of absorbing effective amounts of the composition. Woven or nonwoven synthetic or natural textile sheets may be employed, as well as sheets of flexible foam and paper, i.e., blotting or rice paper. An especially preferred nonwoven fabric is the 75% polyester/25% rayon blend available from Sterns and Foster (Cincinnati, Ohio) and designated 2005-8 (20 oz./yd.), or the 70% polyester/30% rayon blend available from Crown Textile Co. (Philadelphia, Pa., PS-1500).

Preferred foam sheets are those of open-celled foam latexes such as those of acrylic polymers prepared by the additional polymerization of acrylonitrile, alkylacrylonitrile (e.g., methacrylonitrile), and the like and the polymers of ethylenically unsaturated carboxylic acid compounds and the corresponding alkyl esters, such as the addition polymers of acrylic acid, methacrylic acid, methyl acrylate, ethyl acrylate, butyl acrylate, maleic acid, fumaric acid and the like. Suitable foams for use as the sheet component of this invention also include the polyurethane foams prepared from aqueous systems, or extracted urethane polymeric materials. The homopolymers and copolymers of 1,4-diene compounds, such as butadiene, 2-chlorobutadiene, isoprene, neoprene (e.g., chlorinated isoprene latexes) may be employed, as well as polyethylene and natural rubber latexes.

The amount of composition which is applied to the absorbent sheet will vary according to the thickness of the sheet and its absorbent ability. Generally paper on textile sheets require a smaller load of the composition than do foam sheets of the same thickness. For example, a load of composition of about from 5–15 g/ft$^2$ on Crown Textile fabric PS-1500 was found to be sufficient as was a composition load of 10–30 g/ft$^2$ on a 1/16″ thick polyurethane foam sheet.

The cosmetic applicators of the present invention may be prepared which are further strengthened and/or increased in drying power by attaching one face of the impregnated sheet to a water-resistant backing substrate such as towelling, a plastic sheet or the like. Such composite applicators may be used until the composition impregnated thereon is depleted, with a decreased risk of the sheets crumpling or tearing. They are particularly useful as bath mats or towels for drying, moisturizing and deodorizing the feet after bathing or showering.

The following examples are illustrative of the invention but are not intended to be a limitation thereon.

TABLE I

Cosmetic compositions were prepared from the following ingredients.

| INGREDIENT | PARTS BY WEIGHT Examples | | | | |
|---|---|---|---|---|---|
| | A | B | C | D | E |
| Silicone Oil (Dow 344) | 5.0 | 29.7 | 5.0 | 5.0 | 5.0 |
| Procetyl AWS | 2.26 | 2.3 | 2.3 | 2.3 | 2.3 |
| Grillocin H4-77 | 2.00 | 2.0 | 2.0 | 2.0 | 2.0 |
| Crodacol CS-50* | 10.8 | 11.0 | 11.0 | 11.0 | 11.0 |
| Liponate PS-4** | 6.0 | 6.0 | 6.0 | 6.0 | 6.0 |
| Talc | 40.0 | 30.0 | 44.0 | 40.7 | 40.0 |
| Stear-O-Pro (Oat Protein)*** | 15.0 | 15.0 | 15.0 | 15.0 | 15.0 |
| K 9100 RBD Fragrance | 4.0 | 4.0 | 4.0 | 4.0 | 4.0 |
| Finsolv TN | 14.0 | — | 10.7 | 14.0 | 14.0 |
| Necon CPS-100 | 0.74 | — | — | — | — |
| Propyl 4-hydroxy benzoate | 0.10 | — | — | — | — |
| Butyl 4-hydroxy benzoate | 0.05 | — | — | — | — |

*Cetyl/Stearyl Alcohol mixture (Croda Inc., New York, N.Y.) (40% min. Stearyl Alcohol, 90% min. Cetyl Alcohol plus Stearyl Alcohol).
**Pentaerythritol Tetrastearate (Lipo Chemicals, Patterson, N.J.)
***(Beacon CMP Corp., Union City, N.J.)

To prepare the compositions of Examples A–E, all of the ingredients except the fragrance, the silicone oil, the talc and the oat protein were heated and stirred at about 60° C. to form a melt. The temperature of the melt was raised to 70°–75° C. and the silicone oil was added, followed by slow addition of a dry mix of the talc and oat protein particles. The stirred mixture was cooled to about 60° C. and the fragrance was added. The mixture was allowed to cool for 1 hour to 50° C., and then spread onto one side of an 8 × 10.5 inch PS-1500 fabric sheet which had been pre-warmed to 55° C. to a composition load of 9.8 g/ft$^2$ by means of a No. 16 Meyer Rod. Alternatively, the composition of Ex. A was coated onto a warmed 1/16 inch sheet of open-celled polyurethane foam to a load of 20 g/ft$^2$ by means of a stainless steel roller.

The finished cosmetic applicators were not wet or sticky to the touch and possessed a pleasant odor. When the treated sides of the applicators were contacted with wet skin under mild pressure, the applicators became slick and deposited a clear moisturizing film upon the skin along with an even coating of particles of the talc and oat protein absorbent agents. The applicators effectively de-oiled and dried the skin, leaving it smooth and pleasant smelling.

While certain representative embodiments of the invention have been described herein for purposes of illustration it will be apparent to those skilled in the art that modifications therein may be made without departing from the spirit and scope of the invention.

We claim:
1. A method for preparing a substantially dry cosmetic applicator, comprising:
 (a) forming a stirred melt of at least one emollient;
 (b) adding dry absorbent particles of at least one water-insoluble moisture-absorbent agent and at least one water-insoluble oil-absorbent agent to the melt;
 (c) adding fragrance to the melt forming a cosmetic composition;
 (d) cooling the composition; and

(e) applying the composition so as to impregnate a sheet of absorbent material.

2. The method of claim 1 wherein the composition is applied so as to impregnate and overcoat one side of a sheet of nonwoven textile or open-celled foam.

3. The method of claim 1 wherein the emollient melt is formed at about 60–75%C, and wherein the composition is cooled to about 50–55%C and applied to a sheet of absorbent material which has been warmed to about 50–55%C.

4. The method of claim 1, wherein:
the dry absorbent particles comprise 30–65% of the mixture; the water-insoluble oil-absorbent particles are soy or oat protein and the water-insoluble moisture absorbent particles are talc.

5. The method of claim 1, wherein:
the absorbent particles are selected from the group consisting of talc, zeolite, clay, oat protein, soy protein, puffed borax, starch, silica and mixtures thereof.

6. The method recited in claim 1, wherein:
the composition comprises about 10–35% by weight emollient selected from the group consisting of cyclic silicone oil, $C_{12}$–$C_{15}$ linear alkyl benzoates, and mixtures thereof;

about 10–20% by weight of a mixture of pentaerythritol tetrastearate and at least one $C_{12}$–$C_{18}$ fatty alcohol;

about 2–7% by weight of a mixture of a bis-oleoylethanoloxy-substituted-tallow amine salt and a cetylpolyalkoxylate;

about 10–65% by weight of a mixture of particles of talc and oat or soy protein particles;

about 0.5–5% by weight of fragrance; and about 0.5–5% by weight water-soluble deodorizing agent.

* * * * *